United States Patent [19]

Rayburn et al.

[11] 4,269,194
[45] May 26, 1981

[54] CARBON DIOXIDE MEASUREMENT FROM EXPIRED GASES IN A PARTIAL REBREATHING ANESTHESIA CIRCUIT

[76] Inventors: Robert L. Rayburn, 12522 La Manana, San Antonio, Tex. 78233; Robert L. Watson, 4019 Bentway, San Antonio, Tex. 78217; Charles R. Elbel, 632 Ogden La., San Antonio, Tex. 78209; Karl W. Schweickardt, 12914 Cima Linda, San Antonio, Tex. 78233

[21] Appl. No.: 40,056

[22] Filed: May 17, 1979

Related U.S. Application Data

[63] Continuation of Ser. No. 876,997, Feb. 13, 1978, abandoned, which is a continuation-in-part of Ser. No. 840,400, Oct. 7, 1977, Pat. No. 4,188,946.

[51] Int. Cl.$^3$ .............................................. A61B 5/08
[52] U.S. Cl. ..................................... 128/719; 128/635
[58] Field of Search ...................... 128/635, 719, 718; 73/23; 422/83, 84, 119; 324/425, 438

[56] References Cited

U.S. PATENT DOCUMENTS

| | | | |
|---|---|---|---|
| Re. 27,668 | 6/1973 | Soltz et al. | 330/30 D |
| 3,273,122 | 9/1966 | Chandler | 340/146.2 |
| 3,694,734 | 9/1972 | Blackmer | 324/425 |
| 3,710,778 | 1/1973 | Cornelius | 128/635 |
| 3,719,576 | 3/1973 | Macur | 204/195 P |
| 3,895,630 | 7/1975 | Bachman | 128/718 |
| 4,057,478 | 11/1977 | Bruckenstein et al. | 204/195 P |

OTHER PUBLICATIONS

Johns, R. J., "A System For Monitoring Pulmonary Ventilation", *Bio-Med Sciences Instr. 6th Nat. Symp.*, 21-23, 1968, pp. 119-121.
Bystrov. et al., *Instruments & Experimental Techniques*, vol. 17, No. 6, Pt. 2, pp. 1702-1703.

*Primary Examiner*—K. L. Howell
*Attorney, Agent, or Firm*—Gunn, Lee & Jackson

[57] ABSTRACT

A method of determining arterial carbon dioxide tension from mixed expired gases of a patient utilizing a partial rebreathing anesthesia circuit. An electrode is inserted into expired gases of a patient to measure expired carbon dioxide tension. An output signal from the electrode, which indicates expired carbon dioxide tension, has a very high impedance. By reducing the impedance of the output signal, a more usable signal is obtained. Also, the signal must be converted to a relatively linear function, which is then scaled to give a visual indication proportionate to the arterial carbon dioxide tension. The electrode is pre-calibrated by gases having known percentages of carbon dioxide. The scaling factor is included to compensate for differences between the expired carbon dioxide tension and arterial carbon dioxide tension.

7 Claims, 7 Drawing Figures

CARBON DIOXIDE MEASUREMENT FROM EXPIRED GASES IN A PARTIAL REBREATHING ANESTHESIA CIRCUIT

The present application is a continuation of U.S. Patent Application Ser. No. 876,997 filed Feb. 13, 1978, now abandoned, which is a continuation-in-part of U.S. Pat. Application Ser. No. 840,400 filed Oct. 7, 1977, now U.S. Pat. No. 4,188,946, the contents of which are hereby incorporated by reference.

BACKGROUND OF THE INVENTION

The background information and description of the controllable partial rebreathing anesthesia circuit as contained in the incorporated reference is useful in obtaining a full understanding of the present invention; however, such background information will not be repeated herein.

Prior to the present invention, the common method of determining arterial carbon dioxide tension was to draw a specimen of the blood from the artery and take the specimen to a laboratory. In the laboratory, the specimen of blood would be placed in a blood gas analyzer. As part of the blood gas analyzer, the specimen of blood would flow over the end or tip of the Severinghaus electrode. A semipermeable membrane at the tip of the Severinghaus electrode would allow the gases contained in the specimen to penetrate therethrough. Inside of the Severinghaus electrode, the carbon dioxide reacts with a bicarbonate solution ($NaHCO_3$) to give off a hydrogen ion ($H+$). The hydrogen ion diffuses into a glass pH electrode located in the center of the cylindrically shaped Severinghaus electrode. The hydrogen ion creates a voltage potential inside of the pH electrode, which voltage potential has an extremely high impedance, normally in the range of $10^{12}$–$10^{15}$ ohms. Proper shielding for the output of the Severinghaus electrode becomes very critical because of the high impedance. The output is proportional to the carbon dioxide content of the blood.

After the measurement of the blood gases as just described, the results have to be transmitted back to the requesting physician. The typical time delay between the request for blood gas analysis, and getting the analysis back, is approximately 15-20 minutes. One problem that may occur as a result of drawing arterial blood gas specimens is arterial occlusion. Arterial occlusion may cause:

1. Ischemia or loss of fingers and/or thumb; or
2. Loss of function of the small muscles of the hands.

Another problem that may occur is infection at the site of the puncture. Still another major problem associated with arterial lines is air embolism.

An additional advantage of the present invention over prior methods of determining blood gases by taking specimens of blood from an individual's artery is the cost. In cases where numerous blood gas samples are required over a period of time, each of the blood gas samples has the normal high cost associated with laboratory analysis.

In small children, there are numerous problems in the drawing of blood gases, including the inaccessibility of the small blood vessels of the child. In cases where the patient is not under anesthesia at the time, considerable pain is associated with the drawing of blood gases.

Other methods of analyzing carbon dioxide in patients during anesthesia include the use of mass spectrophotometry or capnographs. The disadvantages of mass spectrophotometry are its size and expense. The mass spectrophotometry equipment is not designed for use in the operating room where space is at a premium. In the case of infrared capnographs, the cost is usually prohibitive for use by each and every patient in the operating room. The instrument is likewise large, cumbersome and bulky. It is also not designed to be used in the operating room. In addition, an infrared capnograph analysis of $CO_2$ is influenced by nitrous oxide, which is frequently used in combination with other anesthetics or alone by patients receiving anesthesia, thereby causing error in results obtained.

SUMMARY OF THE INVENTION

It is an object of the present invention to provide a method of determining carbon dioxide tension from mixed expired gases of a patient utilizing a partial rebreathing anesthesia circuit.

To convert an output signal from a $CO_2$ electrode to a continuous readout signal proportionate to the arterial carbon dioxide tension of a patient, a $CO_2$ electrode is immersed in the expired gases from the patient.

The $CO_2$ electrode may be inserted in a control module forming a portion of an anesthesia breathing circuit, which electrode will measure the carbon dioxide tension and give an electrode signal proportionate thereto. The electrode signal must then be converted in the analyzer circuit to a control signal inversely proportionate to fresh gas flow. The analyzer circuit in converting the electrode signal to the control signal also includes an adjustment factor to account for normal variations between arterial carbon dioxide tension in the patient and expired carbon dioxide tension as measured in the control module. By adjusting fresh gas flow, a reciprocal change in the carbon dioxide tension can be obtained.

Within the carbon dioxide analyzer, the electrode signal as received from the electrode has a very high impedance that must be reduced through an impedance converter. Thereafter, because the signal from the impedance converter is still in a logarithmic form, an antilog function must be obtained, which antilog function is inversely related to fresh gases being received by the patient. A scaling factor is included to account for normal differences between arterial carbon dioxide tension and expired carbon dioxide tension as monitored by the electrode. In the present invention after scaling the signal, it may be measured in any predetermined units. For convenience, the present invention gives a visual output through a digital voltmeter, which visual output is given in millimeters of mercury as commonly used by physicians to measure carbon dioxide tension. As an additional feature, the carbon dioxide analyzer is battery operated for ease of usage and equipped with a recharging circuit. Alarms and monitors indicate if the battery voltage is low.

Prior to the use of the $CO_2$ electrode with the carbon dioxide analyzer in an anesthesia breathing circuit, the carbon dioxide analyzer must be calibrated in a calibration chamber. Fresh gas having a predetermined low concentration of $CO_2$ is fed into the calibration chamber and the low scale adjustment in the carbon dioxide analyser is made. Next, by feeding another gas with a high concentration of $CO_2$ into the calibration chamber, the high adjustment of the carbon dioxide analyzer is made.

While the carbon dioxide tension as measured by the $CO_2$ electrode and carbon dioxide analyzer may be given in any particular scale, the readout of the present invention is in millimeters of mercury. Adjustment of the scaling factor is provided in the carbon dioxide analyzer either at the end of the calibration procedure with a known concentration of $CO_2$ in the calibration chamber or after the carbon dioxide tension as monitored by the $CO_2$ electrode has stabilized during the administration of anesthesia.

DESCRIPTION OF THE PREFERRED EMBODIMENT

Figure 1:
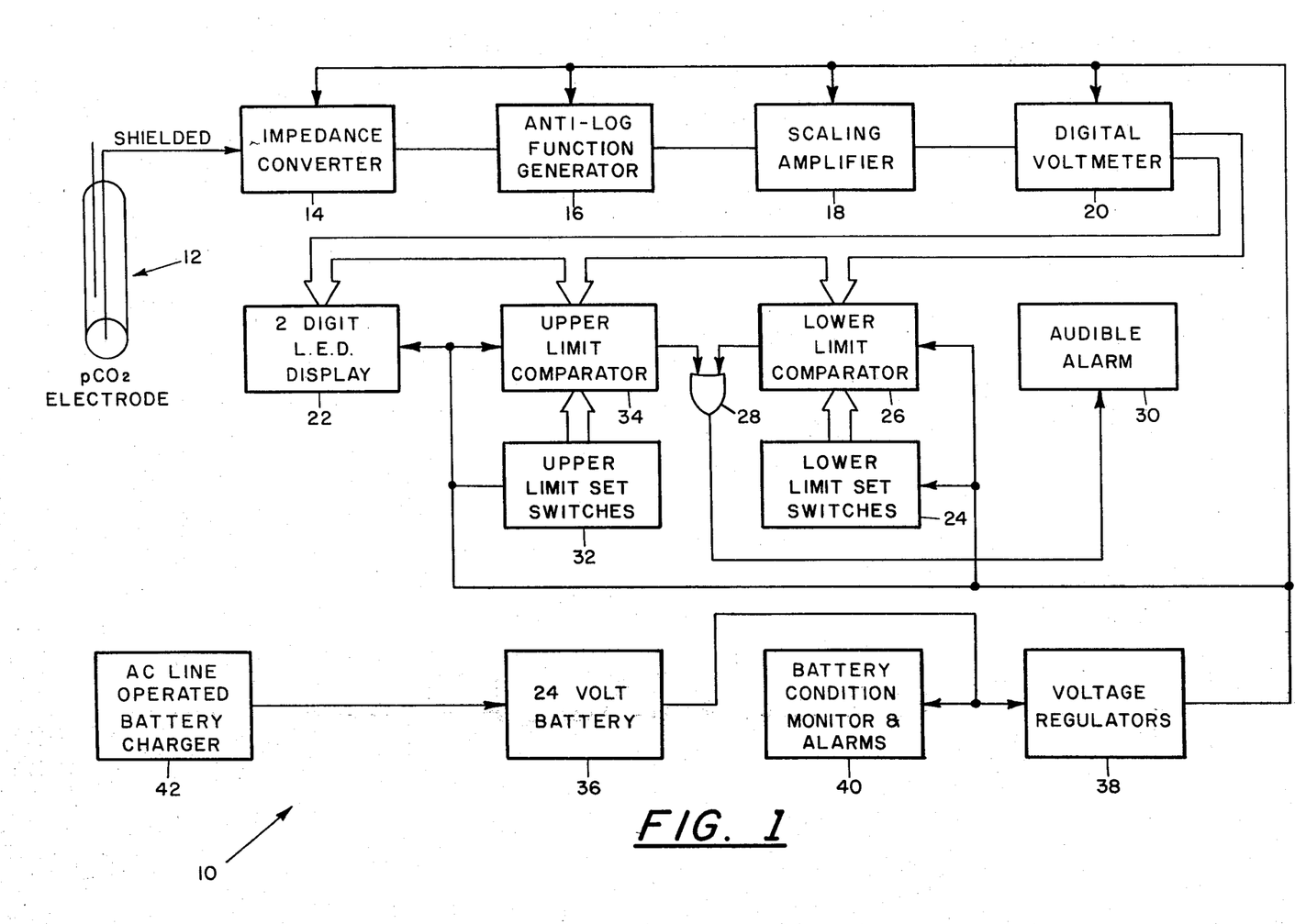
FIG. 1 is a schematic block diagram of a carbon dioxide analyzer for use with a $CO_2$ electrode to form a part of an anesthesia breathing circuit.

Referring first to FIG. 1 of the drawings, there is shown a schematic block diagram 10 of a carbon dioxide analyzer for use in conjunction with the $CO_2$ electrode 12. The letter "p" prior to the designation for carbon dioxide indicates carbon dioxide tension is being measured. The $CO_2$ electrode 12 may be of any commercially available type, such as $CO_2$ electrodes manufactured and sold by Instrumentation Laboratory, Inc. located in Lexington, Mass. The $CO_2$ electrode is commonly referred to as a "Severinghaus" electrode. The Severinghaus electrode has a very high output impedance as will be discussed in more detail hereinafter.

By placing the $CO_2$ electrode 12 in the expired gases from a patient, an electrode voltage is developed that has a very high source impedance, of the order of $10^{12}$–$10^{15}$ ohms. Because of the high impedance, the electrode voltage is shielded as it feeds to an impedance converter 14. Evan inside of the impedance converter 14, the electrode signal is shielded until the impedance of the signal has been changed to a more usable level. The shielding is isolated to prevent the pickup of unwanted noise or interference through the shielding. The impedance converter 14 may use different types of isolation devices including, but not limited to, field effect transistors, as a means for reducing the impedance of the electrode signal to a more usable level.

By having adjustable operational amplifiers as part of the impedance converter 14, the circuit as shown in FIG. 1 can be calibrated as will be explained in more detail subsequently.

An output signal from the impedance converter is fed to an antilog function generator 16. The antilog function generator 16 produces a nonlinear antilogarithmic relationship between its input and output, which relationship is necessary because the electrode voltage developed by the $CO_2$ electrode 12 is logarithmic. Therefore, an antilog function generator is necessary to convert the signal received from the impedance converter 14 to a generally linear form.

The output signal from the antilog function generator 16 is fed to a scaling aplifier 18. The scaling amplifier 18 produces a signal of a more convenient size that may be used by digital voltmeter 20. Also, the scaling amplifier 18 may be externally adjusted as will be explained in more detail subsequently to compensate for temperature or other variables as may exist between the carbon dioxide in contact with the $CO_2$ electrode 12 and the carbon dioxide tension as exists in the patient's bloodstream. This adjustment may be determined experimentally as explained in the incorporated reference.

The output of the scaling amplifier 18 is converted in a digital voltmeter 20 to a digital output. The digital output feeds a two digit light emitting diode display 22 that gives a visual indication of the carbon dioxide tension as measured by the $CO_2$ electrode 12. To insure that the carbon dioxide as measured by the $CO_2$ electrode 12 is within certain limits, lower limit set switches 24 feed a lower limit voltage level into lower limit comparator 26. The lower limit voltage level is representative of the minimum value of carbon dioxide tension that should exist as measured by the $CO_2$ electrode 12. If the value being fed into the lower limit comparator 26 from the digital voltmeter 20 is less than the value being fed into the lower limit comparator 26 by the lower limit set switches 24, an output signal will feed through OR gate 28 to operate an audible alarm 30. It should be realized that the audible alarm 30 may be replaced by any suitable alarm system as operated by the output from OR gate 28.

Likewise, an upper limit set switch 32 feeds an upper limit voltage level into an upper limit comparator 34, which upper limit voltage level is representative of a maximum value of carbon dioxide that should be measured by the $CO_2$ electrode 12 for an individual patient. If the output of the digital voltmeter 20 exceeds the upper limit voltage level as set by the upper limit set switch 32 and fed into the upper limit comparator 34, the upper limit comparator 34 will feed an output signal through OR gate 28 to audible alarm 30. The voltage levels of the upper limit set switch 32 and lower limit set switches 24 may be varied according to the individual patient and the patient's current condition.

A portion of the schematic block diagram 10 as just described hereinabove may be operated off of a battery 36. Battery 36 as described in the preferred embodiment is 24 volts DC. Because the voltage level of the battery 36 may vary, and the previously described portion of the schematic block diagram requires a fairly accurate voltage level, voltage regulators 38 give a regulated voltage output. Also, if battery 36 drops below a preset level, battery condition monitor and alarm 40 will indicate that battery 36 is low. If battery 36 is low as indicated by the battery condition monitor and alarm 40, an AC line operated battery charger 42 may be connected to the battery 36 to recharge the battery to a predetermined level.

Figure 2:
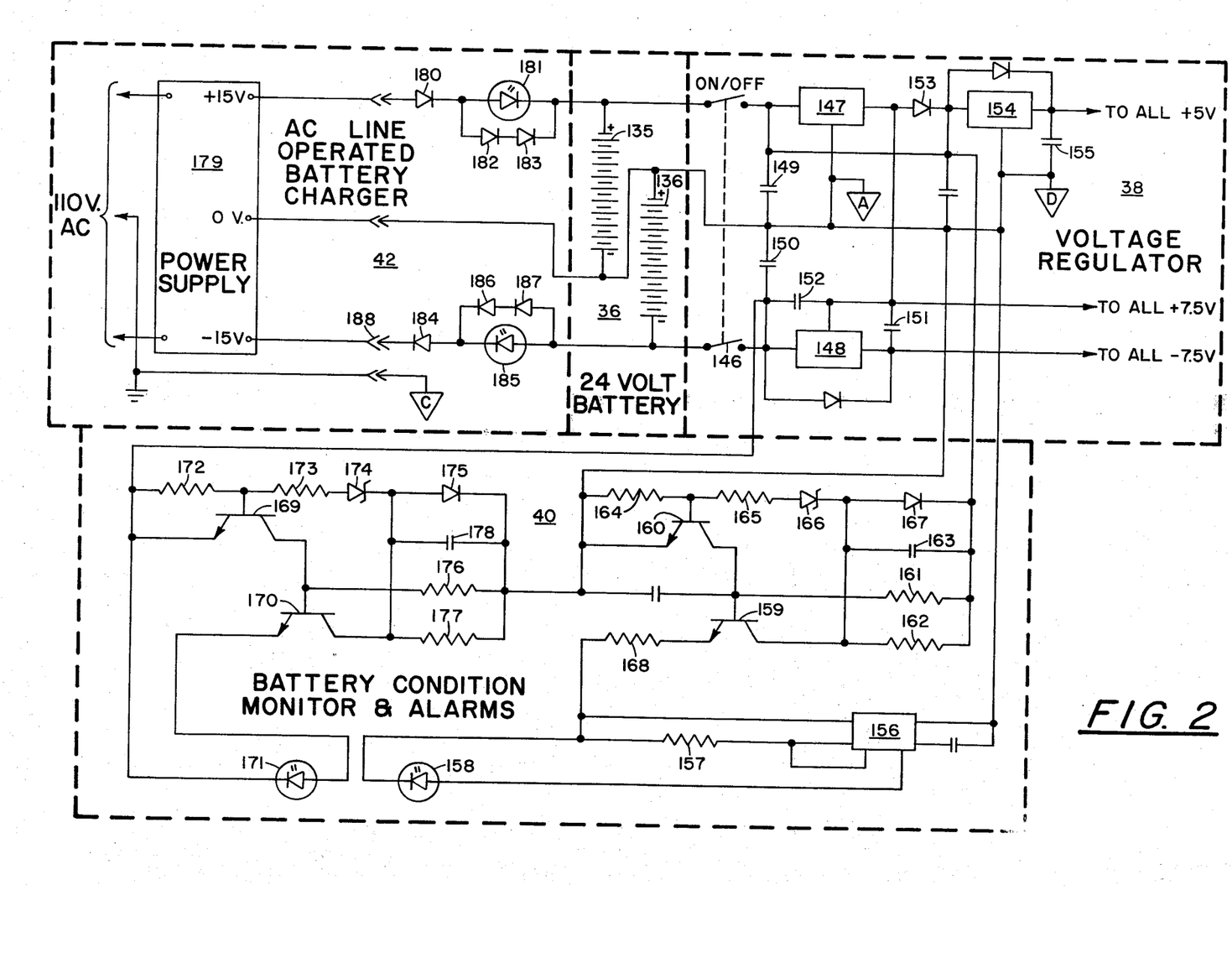
FIGS. 2, 3, 4, 5a and 5b are more detailed schematic diagrams showing one preferred embodiment of FIG. 1.
Figure 3:
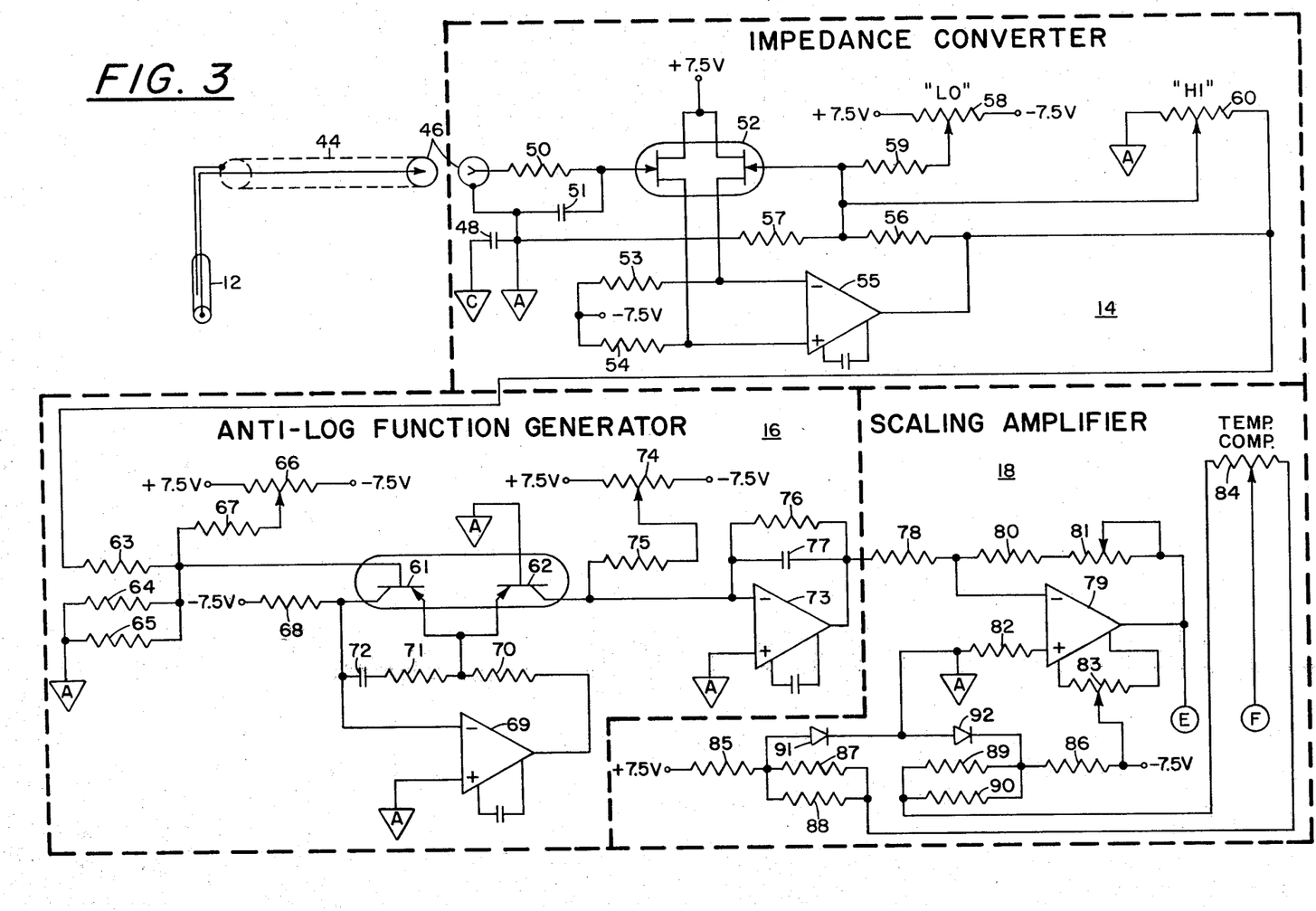
Figure 4:
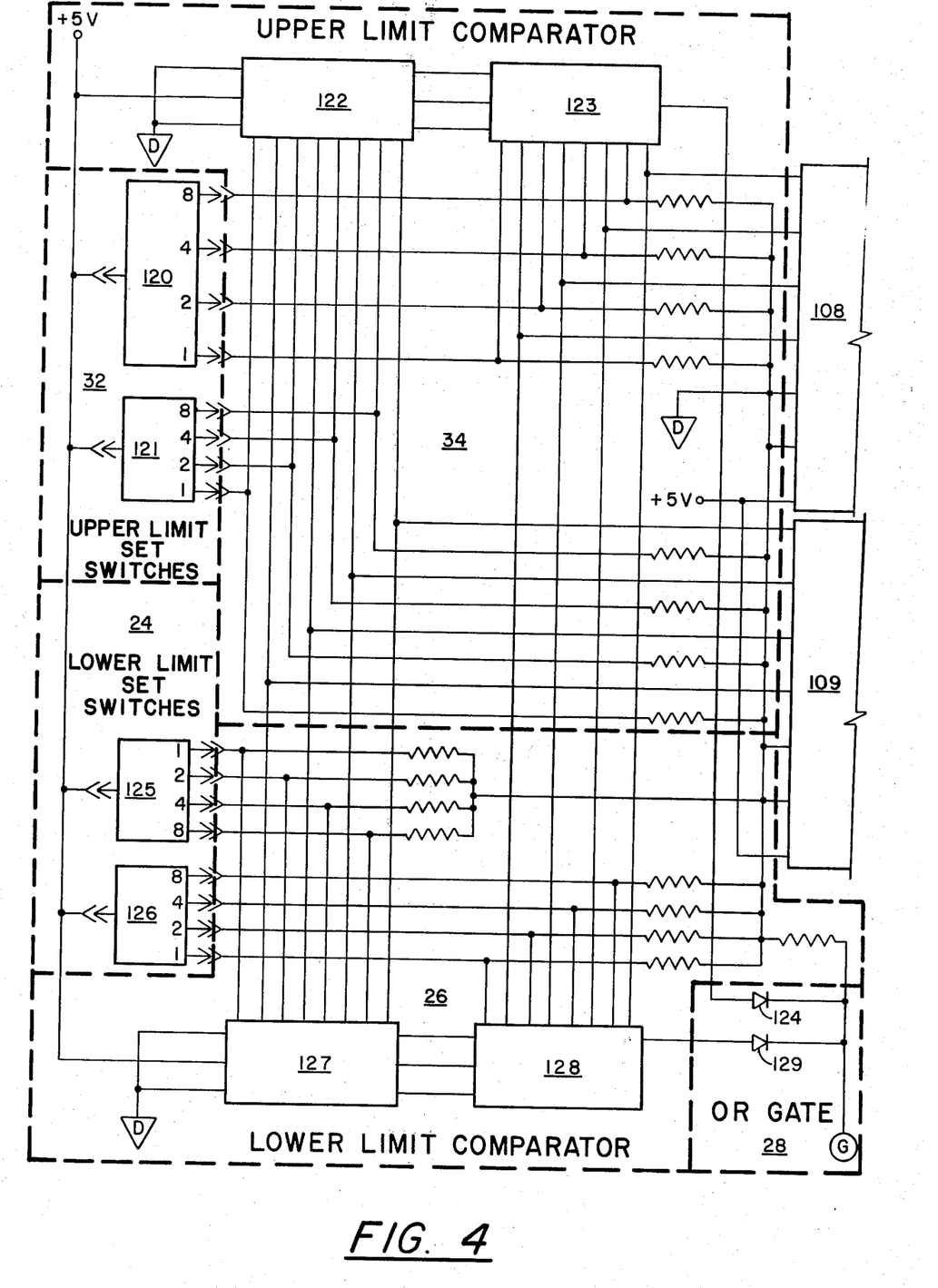

Referring now to FIGS. 2, 3, 4, 5a and 5b in combination, a more detailed schematic diagram of the preferred embodiment is shown. The same blocks as used in the schematic block diagram 10 will be used in conjunction with the descriptions of FIG. 2, 3, 4, 5a and 5b. Individual blocks of the schematic block diagram 10 as included in FIGS. 2, 3, 4, 5a and 5b are as follows:

| FIG. | SCHEMATIC BLOCKS | NO. |
|---|---|---|
| 2 | AC line operated battery charge | 42 |
|   | 24 volt battery | 36 |
|   | Battery condition monitor & alarm | 40 |
|   | Voltage regulators | 38 |
| 3 | Impedance converter | 14 |
|   | Antilog function generator | 16 |
|   | Scaling amplifier | 18 |
| 4 | Lower limit set switches | 24 |
|   | Lower limit comparator | 26 |

Figure 5A:
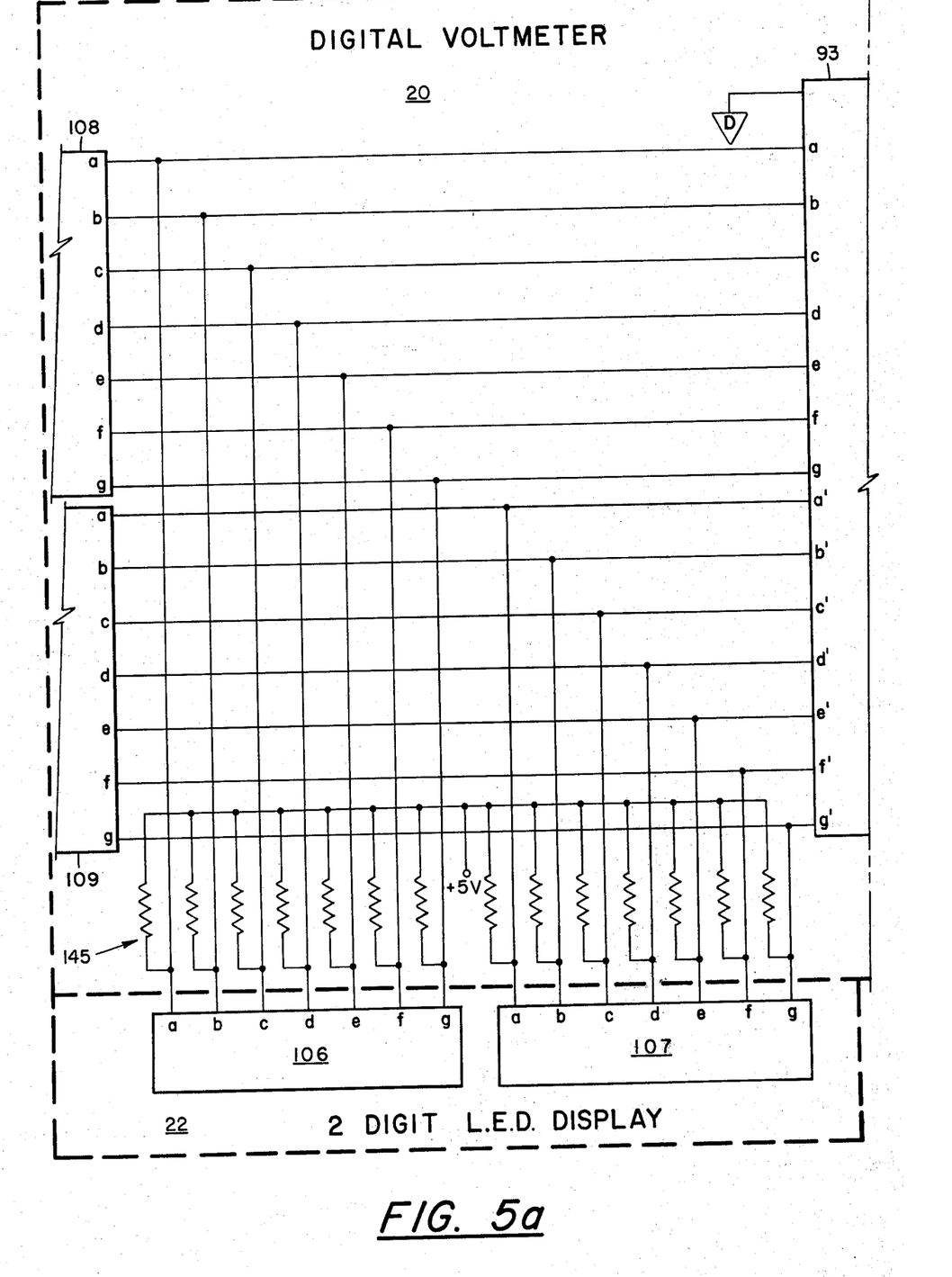
Figure 5B:
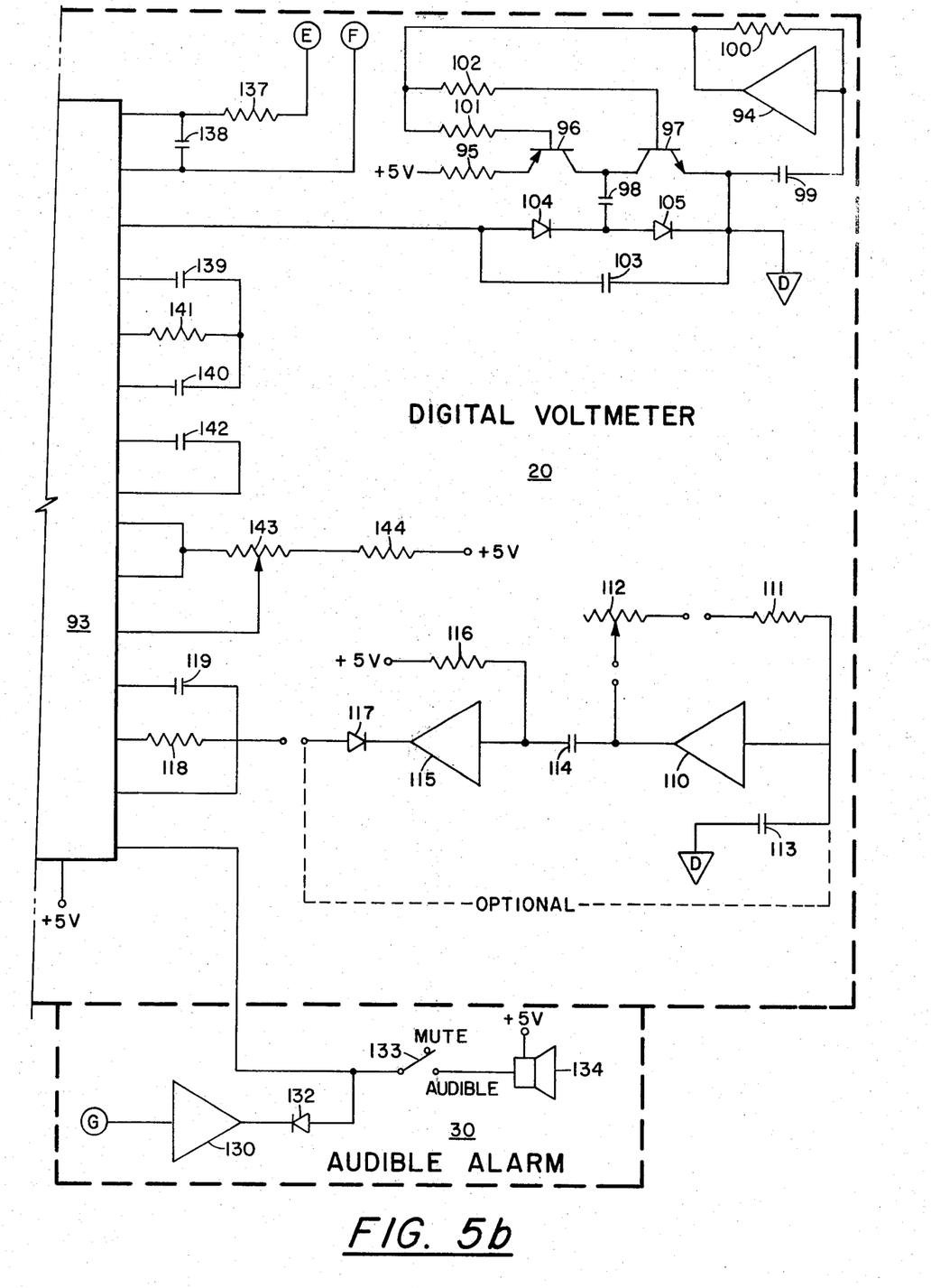

| FIG. | SCHEMATIC BLOCKS | NO. |
| --- | --- | --- |
| | Upper limit set switch | 32 |
| | Upper limit comparator | 34 |
| | OR gate | 28 |
| 5a | Digital voltmeter | 20 |
| | Two digit L.E.D. display | 22 |
| 5b | Digital voltmeter | 20 |
| | Audible alarm | 30 |

Referring now to FIG. 3 of the drawings, the $CO_2$ electrode 12 is connected to the impedance converter 14 by means of shielded cable 44. Even the connector 46 between the shielded cable 44 and the impedance converter 14 is isolated. The isolated connector 46 connects at various points throughout the schematic diagram as point A; however, point A remains isolated from the case (represented throughout as point C) by an isolation capacitor 48. Point A is an isolated or floating ground which can be basically called an "analog" ground. Point D (as will be explained in conjunction with FIG. 4) is also a floating ground commonly referred to as a "digital" ground.

To understand the necessity of the shielding and the floating grounds, a further explanation of the $CO_2$ electrode is necessary. The $CO_2$ electrode 12 is essentially a standard hydrogen ion concentration measuring electrode that has the reference half-cell located therein. The $CO_2$ electrode 12 is internally immersed in a buffer and isolated from gases being measured by a semipermeable membrane. The semipermeable membrane allows gases to penetrate, but not liquids. The $CO_2$ electrode 12 is essentially the same as any other pH measuring electrode in that it has an enormously high output impedance and a very low voltage level. The $CO_2$ electrode 12 acts essentially like a battery whose voltage is determined by the substance in which the electrode is soaking at the moment. In measuring carbon dioxide in exhaled gases, the $CO_2$ electrode 12 normally has an output voltage in the vicinity of 600 millivolts with an output impedance somewhere between $10^{12}-10^{15}$ ohms.

Referring back to the impedance converter 14, isolation of connector 46 is essential to prevent electrical interference. The center conductor of the shielded cable 44 is connected inside the inner shield to resistor 50 and capacitor 51. The resistor 50 should be of a fairly large magnitude in the tens of megohms range. Capacitor 51 may be typically of the polystyrene type within the hundreds of picoFarad range and with a fairly large voltage rating. The function of the RC network is to keep radio frequency interference out of the following circuitry as will be subsequently described. Due to the high input impedance as received from the electrode 12, it is essential that capacitor 51 be as close to an ideal capacitor with no leakage resistance as possible. Due to the high voltage rating and low capacitance of a polystyrene type capacitor, leakage in capacitor 51 is reduced.

From the RC network of resistor 50 and capacitor 51, the signal from electrode 12 is fed to the gate of a dual field effect transistor 52. The drain terminals of the dual field effect transistor 52 are connected to +7.5 volts received from the voltage regulator 38. The source terminals of the dual field effect transistor 52 are connected through resistors 53 and 54 to a −7.5 volts also received from the voltage regulator 38. Resistors 53 and 54, which do not dissipate very much wattage, have a very low amount of drift due to changes in temperature.

Both sections of the dual field effect transistor 52 are matched to a fair degree of accuracy for their operating characteristics. Voltages impressed upon the gates of the dual field effect transistor 52 will determine the current flowing therethrough and consequently the voltage developed across resistors 53 and 54, respectively. The function of the dual field effect transistor 52 is to begin the conversion of the extremely high input impedance down to a lower impedance that can be more easily used.

The first step in converting the extremely high input impedance is the development of a differential voltage across resistors 53 and 54 by the dual field effect transistor 52. The voltage developed across resistors 53 and 54 is fed into operational amplifier 55, which again utilizes field effect transistors therein. The values of resistors 53 and 54 are still very high far as practical integrated circuit amplifiers are concerned. The operational amplifier 55 has a fairly high input impedance and gives an output proportionate to the difference in input received from resistors 53 and 54. Dual field effect transistor 52 also isolates the bias currents generated by the operational amplifier 55 from the electrode 12.

A feedback network from the output of operational amplifier 55 includes resistors 56 and 57. The feedback as received through resistor 56 is fed back into one gate of the dual field effect transistor 52 not connected to the $CO_2$ electrode 12. The feedback to the dual field effect transistor 52 adjusts the operating point of the dual field effect transistor 52 such that the voltage appearing across the inputs of operational amplifier 55 will be very close to the analog ground A. Therefore, if the electrode 12 is giving an output signal, the corresponding voltage as developed across operational amplifier 55 will be very low. Because the characteristics of each dual field effect transistor 52 vary considerably from one unit to another, the feedback loop as used in conjunction with operational amplifier 55 provides a stabilized gain for the overall system. This also provides a temperature compensation of dual field effect transistor 52.

Resistor 57 provides an impedance path to analog ground to develop a voltage thereacross. Resistor 56 simply scales the voltage as developed across resistor 57. The voltage that is developed across resistor 57 is basically the sum of the output of operational amplifier 55 and the dual field effect transistor 52 voltage, plus the voltage that is generated by a low calibration.

The low calibration is provided by variable resistor 58 which connects between +7.5 volts and −7.5 volts. Resistor 58, which is located on the front of a control box as will be subsequently described in more detail, is normally a 50 kilo-ohm 10 turn pot. Resistor 59 is a current limiting resistor connected to the wiper arm of the variable resistor 58. Resistor 58 is used to adjust the overall reading of the entire carbon dioxide analyzers shown in schematic block diagram 10 to agree with the partial pressure of a low concentration calibration gas in which the $CO_2$ electrode 12 is immersed for calibration. The current from the amplifier combination of field effect transistor 52, operational amplifier 55 and variable resistor 58 is summed in resisotr 57. The overall result of adding these currents feeds through resistor 56 from the impedance converter 14 to the antilog function generator 16. Resistor 56 may be selected at the time of assembly of a circuit.

Variable resistor 68, which may be externally adjusted, is essentially in parallel with the resistor 56 and functions to adjust the overall gain of the impedance converter 14. Variable resistor 60 causes the reading on the two digit LED display 22 to agree with the partial pressure of a high calibration gas in which electrode 12 may be immersed. The high calibration pot (variable resistor 60) and the low calibration pot (variable resistor 58) are used in the calibration of the circuit so that the operating point is placed in a known range. The digital voltmeter 20 will then agree for points in between and, to an extent, beyond the low and high calibration points.

The entire circuitry of the impedance converter, with the exception of the low calibration pot 58 and the high calibration pot 60, is contained within a shielded enclosure that may be made of any suitable conductive material, such as aluminum. Due particularly to the extremely high input impedance, the impedance converter 14 is very sensitive to pickup of static fields that exist essentially everywhere. The aluminum enclosure forms an electrostatic shield and is connected to analog ground A. Portions of the circuit as just described in the impedance converter must be extremely clean to avoid leaking currents.

The antilog function generator 16 simply produces a nonlinear relationship between its input and output. This is necessary because of the variation in the electrode voltage from the $CO_2$ electrode 12 versus the concentration of carbon dioxide in a logarithmic relationship. To get a linear partial pressure of $CO_2$, the reciprocal operation of the logarithmic function (antilog) must be performed. Generally speaking, one of the characteristics of a transistor is that the voltage between the base and the emitter is proportional to the logarithm of the current flowing through that junction. This characteristic does vary with temperature. Transistors 61 and 62 (which are dual transistors) of the antilog function generator 16 allow the voltage to be logarithmically varied. By use of a feedback loop and an operational amplifier, the logarithmically varied voltage will appear in an output signal as an antilogarithmic transfer function.

The input voltage received from resistor 56 of the impedance converter 14 feeds through input resistor 63 into the antilog function generator 16. The input resistor 63 is a stable value resistor. Resistors 64 and 65 are temperature compensating resistors used to overcome the second order temperature effect that exists in transistor 61. A dual transistors, such as transistors 61 and 62, is preferred for reasons of temperature compensation. Potentiometer 66 is connected between −7.5 volts and +7.5 volts with the wiper arm being connected through limiting resistor 67 to the base of transistor 61. The current flowing into the base of transistor 61 determines its operating point. The collector of transistor 61 is connected through resistor 68 to −7.5 volts and to an input for operational amplifier 69. The other input for operational amplifier 69 is connected to analog ground A. The output of the operational amplifier 69 connects to the emitters of transistors 61 and 62 in a feedback loop so that instead of being a logarithmic relationship between input voltage and output voltage, it is an analogarithmic function because it is in a negative feedback loop of the operational amplifier 69. Resistors 70 and 71 form a voltage divider network in series with capacitor 72 to give the feedback loop for operational amplifier 69. Resistor 70 is basically a current limiting resistor to prevent overloading of operational amplifier 69. Capacitor 72 and resistor 71 are stabilizing components to prevent operational amplifier 69 from breaking into oscillation if its input signal becomes very small. The output signal from the operational amplifier 69 as fed through resistor 70 supplies emitter current to transistor 62. The output from transistor 62 is fed through an inverting amplifier 73 to give an output signal. Connected to the collector output of transistor 62 is potentiometer 74 connected between −7.5 volts and +7.5 volts. The wiper arm of potentiometer 74 is connected through resistor 75 to the input of operational amplifier 73 to remove any offset voltages that may exist. Potentiometer 74 and resistor 75 cancel out or get rid of any offset voltages. Resistor 76 and capacitor 77 provide a feedback path for operational amplifier 73.

The scaling amplifier 18 receives the output from inverting amplifier 73 of the antilog function generator 16 through input resistor 78. The scaling amplifier 18 has two basic functions, the first of which is to produce a signal of a convenient size for the digital voltmeter 20. The second function is to provide an arithmetic addition to the value of the voltage that is fed to the digital voltmeter 20. The arithmetic addition to the voltage level is necessary to overcome membrane diffusion problems at the electrode 12, as well as to account for other variances between the carbon dioxide tension as measured by electrode 12 and arterial carbon dioxide tension. The input signal feeds through input resistor 78 into operational amplifier 79, gain of which is controlled by input resistor 78, resistor 80 and variable resistor 81. Variable resistor 81 adjusts the gain to the precise value that is required. Once variable resistor 81 has been adjusted, it should not be varied further, except at the factory. Adjustments of variable resistor 81 can only be made internally. Resistor 82, which connects between the other input of operational amplifier 79 and analog ground A, provides a bias current cancellation function. Potentiometer 83 provides the offset adjustment for the operational amplifier 79. The wiper of potentiometer 83 is connected to −7.5 volts, which is a normal way for connecting operational amplifier 79.

Potentiometer 84, which is on the front of the control panel and labeled "TEMP COMP", is a compensation potentiometer used to compensate for temperature or other variations as may exist between carbon dioxide tension measured by the electrode 12 and arterial carbon dioxide tension. The function of the potentiometer 84 is to apply a fixed arithmetic addition or subtraction to the actual partial pressure carbon dioxide tension reading of electrode 12. Normally, the value of potentiometer 84 is approximately 500 ohms and has approximately 10 turns. The voltage as applied to potentiometer 84 is temperature stabilized and connected between +7.5 volts and −7.5 volts. Resistors 85 and 86 simply serve to limit the current from +7.5 volts and −7.5 volts, respectively. The voltage sources (+7.5 volts and −7.5 volts) as connected through current limiting resistors 85 and 86, respectively, are also connected to analog ground A through diodes 91 and 92, respectively. Resistors 87, 88, 89 and 90 serve to scale the voltage developed across diodes 91 and 92 as it is applied to the ends of variable resistor 84. The operating current of diodes 91 and 92 is chosen such that their temperature characteristics will be the opposite of the temperature offset of operational amplifier 79. As an approximate value, approximately 225 millivolts will be developed across diodes 91 and 92, respectively. The voltages developed across diodes 91 and 92, which are of opposite sign, are applied to the ends of the temperature compensating resistor (potentiometer 84) via resistors 87, 88, 89 and 90. If the temperature of the environment does change, the change in voltages across diodes 91 and 92 will be of an opposite sign to compensate for the changes of the operational amplifier 79. The temperature compensating resistor 84 is also used to compensate for other factors that may cause a variation between the reading by electrode 12 and actual arterial carbon dioxide tension. As was discussed in the incorporated reference, the normal adjustment is approximately 5 millimeters of mercury for an adult as controlled by temperature compensating resistor 84. The output from the temperature compensating resistor 84 and the scaling amplifier 18 is fed to digital voltmeter 20 shown in FIGS. 5a and 5b through connections E and F.

Referring to FIG. 5a of the drawings, connections E and F of the digital voltmeter 20 receive the output from the scaling amplifier 18. The signal as received in the digital voltmeter 20 is fed into integrated circuit logic 93, which is essentially an integrated circuit digital voltmeter which may be commercially purchased as one component with a few peripheral components connected thereto. Voltage generating source 94 converts the +5 volts that it is connected to by resistor 95 via transistors 96 and 97, both of which act as amplifiers to charge capacitor 98 to a negative voltage. The integrated circuit logic 93 requires a negative voltage of approximately −5 volts. The voltage generating source 94 is caused to oscillate by capacitor 99 and resistor 100. The output of the voltage doubler generating source 94 is applied to the base of transistors 96 and 97 by resistors 101 and 102, respectively. The oscillating output from the voltage generating device 94 applies a varying voltage to the combination of capacitors 98 and 103 via diodes 104 and 105. Diodes 104 and 105 with capacitors 98 and 103 are connected into a voltage network with the negative output being connected to a digital ground. A DC output voltage of approximately −5 volts is then applied to the integrated circuit logic 93.

The integrated circuit logic 93 is one integrated circuit chip that performs an analog to digital conversion. A typical such integrated circuit logic is manufactured by Intersil and labeled "ICL 7107". The integrated circuit logic 93 is intended to drive seven segment light emitting diode displays in a conventional manner. The inputs to the integrated circuit logic 93 from connections E and F are received through a low pass filter formed by resistor 137 and capacitor 138. Also, capacitor 139 and 140 in conjunction with resistor 141 provide an integrator time constant for integrated circuit logic 93. Capacitor 142 provides a stable reference capacitance. Potentiometer 143 and resistor 144 provide an adjustment for calibrating the integrated circuit logic 93.

Outputs a-g of the integrated circuit logic 93 drive seven segment display 106 of the two digit light emitting diode display 22. Likewise, outputs a'-g' drive seven segment display 107, which also forms a part of the two digit light emitting diode display 22. Resistors 145 are pull-up resistors for the lines driving seven segment displays 106 and 107 and integrated circuits 108 and 109. Also, outputs a-g of the integrated circuit logic 93 are applied to the inputs of binary coded decimal (BCD) converter 108. Likewise, outputs a'-g' of integrated circuit logic 93 are applied to the inputs of BCD converter 109. A typical such BCD converter is manufactured by National Semiconductor and given numerical designation "74C915".

If the output of the electrode 12 is changing fairly rapidly thereby creating readability difficulties in the two digit LED display 22, a sample and hold is provided by optional circuitry for the integrated circuit logic 93. Included in the optional circuitry is a feedback oscillator 110 whose time constant is determined by resistor 111, potentiometer 112 and capacitor 113. By adjusting the potentiometer 112, the frequency of the feedback oscillator may be varied. The frequency of the feedback oscillator 110 can be varied from 6 cycles per second to 0.2 cycles per second, which frequency corresponds to the sample rate. The output of feedback oscillator 110 connects through coupling capacitor 114 to oscillator 115 and resistor 116. The output from oscillator 115 is fed through diode 117 and RC time constant provided by resistor 118 and capacitor 119 to the integrated circuit logic 93 to give a clock input.

Referring now to the upper limit set switch 32 as shown in FIG. 4, a digital value output is given in a binary coded form. Mechanical switch 120 sets in the most significant digit and mechanical switch 121 sets in the least significant digit in the upper limit set switches 32. The binary outputs of switches 120 and 121 are fed into the upper limit comparator 34. The output from the upper limit set switches 32 are compared with the outputs of the BCD converters 108 and 109 in the digital voltmeter 20. The comparison is done by comparators 122 and 123 in upper limits comparators 34. If the value received from the BCD converters 108 and 109 is larger than the value received from the upper limit set switches 120 and 121, the output from comparator 123 is fed to the audible alarm 30 through connection G via diode 124 in OR gate 28.

The lower limit set switches 24, which include mechanical switches 125 and 126, perform a very similar function. Mechanical switch 126 is for the most significant digit and mechanical switch 125 is for the least significant digit. Mechanical switches 125 and 126 generate a binary coded decimal value as set in by the operator as a lower limit. A comparison is then made in the lower limit comparator 26 by means of comparators 127 and 128. If the value generated by BCD converters 108 and 109 is less than the value generated by switches 125 and 126, an output is given from comparator 128 through diode 129 of the OR gate 28 to the audible alarm 30 via connection G.

Figure 6:
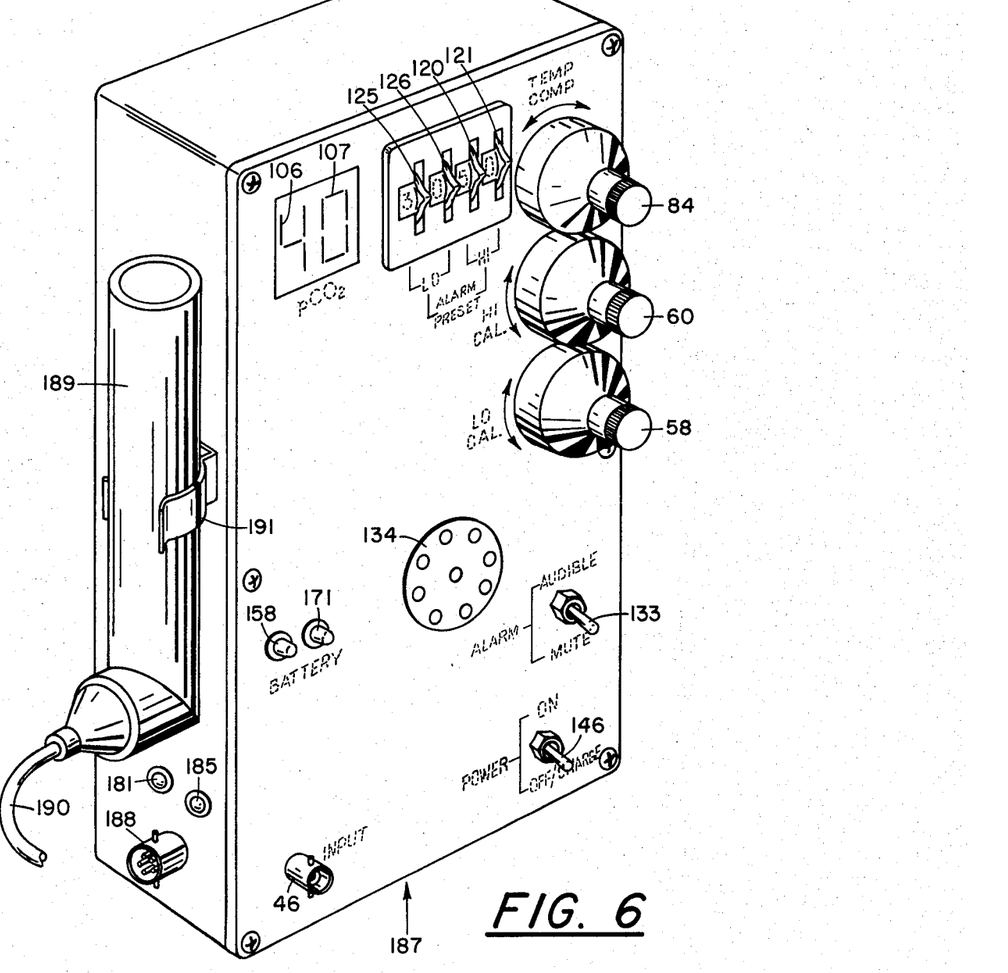
FIG. 6 is a front perspective view of a control box containing the carbon dioxide analyzer.

The unmarked resistors as contained in the upper limit comparator 34 and lower limit comparator 26 are pull-up resistors to establish desired voltage levels. While it is not shown in the detail schematic, switches 120 and 121 of the upper limit set switches 32 may be connected to visual displays as shown in FIG. 6 adjacent thereto. The same is true for switches 125 and 126 of lower limit set switches 24.

Referring now to the audible alarm in FIG. 5b, either of two inputs will cause the audible alarm in FIG. 5b to function. An input is received from either diodes 124 or 129 of OR gate 28 indicating either the upper limit has been exceeded or the lower limit is not exceeded and will activate the alarm via inverter 130. The output from the inverter 130 is transmitted via diode 132 and switch 133 to the alarm 134. The alarm itself may be of any commercial type, such as a Mallory Sonalert. Switch 133, which is on the front control panel, either enables the alarm by being in the "audible" position, or disables the alarm by being in the "mute" position.

Referring now to FIG. 2 of the drawings, a 24 volt battery 36 is provided by series connections of 12 volt batteries 135 and 136. The opposing sides of batteries 135 and 136 are fed through ON/OFF switch 146 located on the front of the control box. The ON/OFF switch 146 is a double-pole double-throw switch. The positive side of battery 135 connects through ON/OFF switch 146 to an +8 volt regulator 147. The negative side of battery 136 connects through the opposite side of ON/OFF switch 146 to the −15 volt regulator 148. A center connection between batteries 135 and 136 also connects through filter capacitors 149 and 150 to regulators 147 and 148, respectively. By combining the outputs of the +8 volt regulator 147 and the −15 volt regulator 148, both of which have a 10% selectability, a −7.5 volts can be obtained. The −7.5 volts is filtered by capacitor 151. Also, filter capacitor 152 is connected between the negative input from the batteries 135 and 136, and +7.5 volts.

The +7.5 volts, which is regulated, is also fed through diode 153 to +5 volt regulator 154. Capacitor 155 provides filtering for the +5 volt output as connected to the digital circuitry.

Battery condition monitor and alarms are connected to the interconnection between batteries 135 and 136, which connection feeds into oscillator 156. Oscillator 156 will give a periodic output causing current to flow through resistor 157 and light emitting diode 158 if voltage developed by battery 135 drops below a predetermined point. The flowing of current through light emitting diode 158, which is visible on the front of the control box, will cause the light emitting diode 158 to periodically illuminate. Extra amplification for driving light emitting diode 158 is obtained by transistors 159 and 160. The time constant as set into oscillator 156 is controlled by resistors 161 and 162 and capacitor 163. Resistors 164 and 165, zener diode 166 and diode 167 provide biasing for transistors 160 and 159. Resistor 168 is a limiting resistor to prevent excess current from flowing through light emitting diode 158.

If the condition of the battery 136 decays beyond a predetermined point, transistor 169 will turn OFF and transistor 170 will be turned ON thereby causing current to flow through light emitting diode 171 contained on the front of the control box. Resistors 172 and 173, zener diode 174 and diode 175 provide biasing for transistor 169. Coupling and biasing are provided by resistors 176 and 177 and capacitor 178.

By use of the battery condition monitor and alarms 40 as just described, light emitting diode 158 will periodically illuminate if the battery 135 drops below a predetermined level. Since battery 135 has more of a drain than battery 136, if battery 136 is discharged below the same predetermined level, light emitting diode 171 will be illuminated continuously.

Upon the 24 volt battery 36 (formed by combining batteries 135 and 136) dropping below a predetermined level, power supply 179 which is connected to a 110 volt AC outlet may be connected to the 24 volt battery 36 in the manner as shown in FIG. 2 by connector 188. Diode 180 insures current flow in the proper direction for the charging of battery 135. Light emitting diode 181 will indicate that battery 135 is being charged. Series diodes 182 and 183 connected in parallel with light emitting diode 181 prevent excessive current flow through light emitting dioe 181. Likewise, diode 184 insures the proper direction of current flow in the charging of battery 136. Light emitting diode 185 indicates that current is flowing to charge battery 136. Again, series diodes 186 and 187 prevent excessive current flow through light emitting diode 185. As long as current is flowing in the charging of battery 136, light emitting diode 185 will illuminate.

Referring to FIG. 6, the light emitting diodes 181 and 185 that will light as long as batteries 135 and 136, respectively, are being charged as shown on the side of the control box 187. The connector 188 for connecting the power supply 179 to the 24 volt battery 36 is also shown on the side of the control box 187.

Other component parts previously described hereinabove that may be reached from the external portion of the control box 187 are shown and indicated in FIG. 6 by like numerals. Also, a calibration chamber 189 in which the electrode 12 may be inserted is shown. Conduit 190 may be connected to a known percentage carbon dioxide gas for the low and high calibrations as previously described. Bracket 191 is a matter of convenience for holding the calibration chamber 189 on the side of control box 187.

We claim:

1. A method of determining arterial carbon dioxide tension from mixed expired gases of a patient utilizing a partial rebreathing anesthesia circuit consisting of the following steps:
   measuring continuously carbon dioxide tension of said mixed expired gases with an electrode inserted therein, an output of said electrode having a high impedance;
   converting said high impedance of said elecrode output in an impedance converter to a lower impedance level;
   shielding and isolating said electrode output until conversion to said lower impedance;
   generating an antilog function from said lower impedance level of said electrode output;
   scaling said anilog function to account for variations between carbon dioxide tension of said mixed expired gases and said arterial carbon dioxide tension, to give a scaled output signal directly related to said arterial carbon dioxide tension, said variations including an arthmetic addition to said antilog function to give said scaled output signal thereby accounting for diffusion, mixing and temperature variations.

2. The method of determining arterial carbon dioxide tension as given in claim 1 including a first step of calibrating said electrode output with said electrode being immersed in known percentages of carbon dioxide.

3. The method of determining arterial carbon dioxide tension as given in claim 2 wherein said calibrating step includes immersing said electrode in a lower percentage carbon dioxide gas and making a low calibration adjustment, and immersing said electrode in a higher percentage carbon dioxide gas and making a high calibration adjustment.

4. The method of determining arterial carbon dioxide tension as given in claim 1 including a further step of continuously monitoring said scaled output signals by a monitoring device.

5. The method of determining arterial carbon dioxide tension as given in claim 4 includes setting upper and lower limits into said monitoring device to give an alarm if said scaled output signal varies outside said upper and lower limits, said upper and lower limits defining a range over which said arterial carbon dioxide tension may vary.

6. The method of determining arterial carbon dioxide tension as given in claim 5 wherein said monitoring device further comprises converting said scaled output signals to a visual display on a digital voltmeter.

7. The method of determining arterial carbon dioxide tension as given in claim 6 includes providing regulated voltages from a battery source to operate previously mentioned components.

* * * * *